United States Patent
Chickering, III et al.

(10) Patent No.: US 6,921,458 B2
(45) Date of Patent: Jul. 26, 2005

(54) METHODS AND APPARATUS FOR MAKING PARTICLES USING SPRAY DRYER AND IN-LINE JET MILL

(75) Inventors: Donald E. Chickering, III, Framingham, MA (US); Sridhar Narasimhan, Framingham, MA (US); David Altreuter, Brookline, MA (US); Paul Kopesky, Quincy, MA (US); Mark Keegan, Andover, MA (US); Julie A. Straub, Winchester, MA (US); Howard Bernstein, Cambridge, MA (US)

(73) Assignee: Acusphere, Inc., Watertown, MA (US)

( * ) Notice: Subject to any disclaimer, the term of this patent is extended or adjusted under 35 U.S.C. 154(b) by 0 days.

(21) Appl. No.: 10/752,861

(22) Filed: Jan. 7, 2004

(65) Prior Publication Data

US 2004/0134091 A1 Jul. 15, 2004

Related U.S. Application Data

(62) Division of application No. 10/324,943, filed on Dec. 19, 2002.

(51) Int. Cl.$^7$ ................................................ B01D 1/16
(52) U.S. Cl. ..................... 159/48.1; 264/12; 159/4.01
(58) Field of Search ......................... 34/360, 424, 576, 34/591, 165; 159/4.01, 48.1; 264/11, 12, 13, 14; 241/5, 59

(56) References Cited

U.S. PATENT DOCUMENTS

| | | | |
|---|---|---|---|
| 4,917,309 A | * | 4/1990 | Zander et al. ................. 241/5 |
| 5,518,709 A | | 5/1996 | Sutton et al. |
| 5,518,998 A | | 5/1996 | Backstrom et al. |
| 5,582,779 A | | 12/1996 | Gross et al. |
| 5,656,299 A | | 8/1997 | Kino et al. |
| 5,667,927 A | | 9/1997 | Kubota et al. |
| 5,741,478 A | | 4/1998 | Osborne et al. |
| 5,853,698 A | | 12/1998 | Straub et al. |
| 5,952,008 A | | 9/1999 | Backstrom et al. |
| 5,957,848 A | | 9/1999 | Sutton et al. |

(Continued)

OTHER PUBLICATIONS

Alamzad, "How to Dry Bulk Material Effectively," *Process Heating*, http://www.process-heating.com/CDA/ArticleInformation/BNP__Features__Item/0,3156,79227,00.html.

Cheng, et al., "Use of a jet mill for dispersing dry powder for inhalation studies," *Am. Ind. Hyg. Assoc. J.* 46:449–454 (Aug. 1985) (abstract only).

Crown Milling Flash Dryer, Product Literature, http://www.crowniron.com/milling.html.

(Continued)

*Primary Examiner*—Henry Bennett
*Assistant Examiner*—Camtu Nguyen
(74) *Attorney, Agent, or Firm*—Sutherland Asbill & Brennan LLP (57) ABSTRACT

Methods and apparatus are provided for making particles comprising: (a) spraying an emulsion, solution, or suspension, which comprises a solvent and a bulk material (e.g., a pharmaceutical agent), through an atomizer and into a primary drying chamber, having a drying gas flowing therethrough, to form droplets comprising the solvent and bulk material dispersed in the drying gas; (b) evaporating, in the primary drying chamber, at least a portion of the solvent into the drying gas to solidify the droplets and form particles dispersed in drying gas; and (c) flowing the particles and at least a portion of the drying gas through a jet mill to deagglomerate or grind the particles. By coupling spray drying with "in-line" jet milling, a single step process is created from two separate unit operations, and an additional collection step is advantageously eliminated. The one-step, in-line process has further advantages in time and cost of processing.

17 Claims, 3 Drawing Sheets

U.S. PATENT DOCUMENTS

| | | | |
|---|---|---|---|
| 5,992,773 | A | 11/1999 | Schwechten |
| 6,015,546 | A | 1/2000 | Sutton et al. |
| 6,022,525 | A | 2/2000 | Sutton et al. |
| 6,022,564 | A | 2/2000 | Takechi et al. |
| 6,045,913 | A | 4/2000 | Castle |
| 6,068,600 | A | 5/2000 | Johnson et al. |
| 6,096,339 | A | 8/2000 | Ayer et al. |
| 6,117,455 | A | 9/2000 | Takada et al. |
| 6,132,699 | A | 10/2000 | Bernstein et al. |
| 6,165,976 | A | 12/2000 | Backstrom et al. |
| 6,199,607 | B1 | 3/2001 | Trofast |
| 6,223,455 | B1 | 5/2001 | Chickering, III et al. |
| 6,228,401 | B1 | 5/2001 | James et al. |
| 6,254,981 | B1 | 7/2001 | Castle |
| 6,308,434 | B1 | 10/2001 | Chickering, III et al. |
| 6,395,300 | B1 | 5/2002 | Straub et al. |
| 6,423,345 | B2 | 7/2002 | Bernstein et al. |
| 6,443,376 | B1 | 9/2002 | Huang et al. |
| 2003/0037459 | A1 | 2/2003 | Chickering, III et al. |
| 2003/0053960 | A1 | 3/2003 | Heijerman et al. |
| 2003/0236238 | A1 | 12/2003 | Trofast et al. |

OTHER PUBLICATIONS

Friedrich, "Size reduction overview: Shear, compression, and impact," *Powder and Bulk Engineering*, http://www.powderbulk.com/main/archive/06_june_01/hosakawa.html.

GEA Niro Inc., Product Literature, "Flash Dryers—A Family of Drying Systems,"http://www.niroinc.com/html/chemical/cflashtech.html.

Hosokawa, Product Literature, "Micron Powder Systems, Mikro–LGM Long Gap Mill" (five pages).

Hosokawa, Product Literature, "Powder and Particle Processing, Mills for Size Reduction" (3 pages).

"Hosokawa Micro Powder Systems Provides Total Solutions for the Pharmaceutical Industry," (Jun. 2000).

Hosokawa Alpine Aktiengesellschaft, Product Literature BA 1196/1 E (10 pages).

Hosokawa, Powder and Particle Processing, Product Literature, Alpine AS Spiral Jet Mill, http://www.hosokawa.com/web/powderequip/SPIRALJETMILL.htm.

Hosokawa, Powder and Particle Processing, Product Literature, Alpine AFG Fluidized Bed Opposed Jet Mills, http://www.hosokawa.com/web/powderequip/AFG.htm.

Hosokawa, Powder and Particle Processing, Product Literature, Alpine Toner TSP High Efficiency Toner Classifier, http://www.hosokawa.com/web/powderequip/TSP.htm.

Hosokawa, Powder and Particle Processing, Product Literature, Mikro–Classifier CC, http://www.hosokawa.com/web/powderequip/MIKROCC.htm.

Hosokawa, Powder and Particle Processing, Product Literature, Vrieco–Nauta Vacuum Dryers, http://www.hosokawa.com/web/powderequip/VACDRYERS.htm.

Hosokawa, Powder and Particle Processing, Product Literature, Micron Dryer / Grinder / Classifier, http://www.hosokawa.com/web/powderequip/MICRONDRYER.htm.

Hosokawa, Powder and Particle Processing, Product Literature, Pulvocron Grinder / Dryer, http://www.hosokawa.com/web/powderequip/PULVOCRON.htm.

Ito, et al., "Effect of pulverization on dehydration behavior of crystals of GK–128, a serotonin3 receptor antagonist," *J. Pharm. Sci.* 85:1117–1122 (Oct. 1996) (abstract only).

Thermalet, Product Literature, http://www.fluidenergype.com/htm/tps_index.htm.

Wennerstrum, et al., "Size reduction solutions for hard–to–reduce materials," *Powder and Bulk Engineering*, http://www.powderbulk.com/main/archive/01_january_02/fitzpatrick.html.

Perry's Chemical Engineers' Handbook, $7^{th}$ Edition, pp 20–22 to 20–56 (1997).

* cited by examiner

METHODS AND APPARATUS FOR MAKING PARTICLES USING SPRAY DRYER AND IN-LINE JET MILL

CROSS-REFERENCE TO RELATED APPLICATIONS

This is a divisional of U.S. application Ser. No. 10/324,943, filed Dec. 19, 2002, now pending. That application is incorporated herein by reference in its entirety.

BACKGROUND OF THE INVENTION

This invention is generally in the field of process equipment and methods for making particles, and more particularly to methods of deagglomerating or grinding spray dried particles.

Spray drying is commonly used in the production of particles for many applications, including pharmaceuticals, food, cosmetics, fertilizers, dyes, and abrasives. Spray drying can be tailored to create a wide spectrum of particle sizes, including microparticles. Spray dried particles are useful in a variety of biomedical and pharmaceutical applications, such as the delivery of therapeutic and diagnostic agents, as described for example in U.S. Pat. No. 5,853,698 to Straub et al.; U.S. Pat. No. 5,855,913 to Hanes et al.; and U.S. Pat. No. 5,622,657 to Takada et al. For these applications, microparticles having very specific sizes and size ranges often are needed in order to effectively deliver the active agents.

Particles may tend to agglomerate during their production and processing, thereby undesirably altering the effective size of the particles, to the detriment of the particle formulation's performance and/or reproducibility. In other circumstances, the particles made may simply be larger than desired for a particular application. Therefore, after they are produced, particles may require additional processing for size reduction and/or deagglomeration.

In one common approach, separate batch process steps are used. For example, particles are made by a known spray drying process, collected, and then ground in a second, separate step. Such a batch method, however, undesirably requires the use of a transfer step from the spray dryer to the mill, which, for an aseptic process, may be difficult to perform. Such a batch process also requires two separate collection steps that are both associated with a yield loss. It would be desirable to provide a sterile particle production and milling process and to minimize product yield losses, reduce material transfer steps, reduce process time, and reduce production costs. In addition, laboratory scale methods for producing microparticle pharmaceutical formulations may require several steps, which may not be readily or efficiently transferred to larger scale production. It would be desirable for the microparticle production and deagglomeration (or grinding) process to be adaptable for efficient, cost effective, commercial scale production.

SUMMARY OF THE INVENTION

Methods and apparatus are provided for making particles in an in-inline process comprising: (a) spraying an emulsion, solution, or suspension, which comprises a solvent and a bulk material, through an atomizer and into a primary drying chamber having a drying gas inlet, a discharge outlet, and a drying gas flowing therethrough, to form droplets comprising the solvent and the bulk material, wherein the droplets are dispersed in the drying gas; (b) evaporating, in the primary drying chamber, at least a portion of the solvent into the drying gas to solidify the droplets and form particles dispersed in the drying gas, the particles dispersed in the drying gas being a feedstream; and (c) flowing the particles of the feedstream through a jet mill to deagglomerate or grind the particles. This process using spray drying coupled with "in-line" jet milling eliminates an aseptic transfer from the spray dryer to the jet mill (which would be particularly important for making pharmaceutical formulations comprising the particles) and an additional collection step that would be associated with a yield loss. The inline process can effectively cut processing time by at least one half compared to a two step process.

In a preferred embodiment of the method, step (c) is conducted to deagglomerate at least a portion of agglomerated particles, if any, while substantially maintaining the size and morphology of the individual particles. Alternatively, step (c) can be conducted to grind the particles.

Preferably, the feedstream of step (b) is directed through a particle concentration means to separate and remove at least a portion of the drying gas from the feedstream. In one embodiment, the particle concentration means comprises a cyclone separator. In one embodiment, the cyclone separates between about 50 and 100 vol.% of the drying gas from the particles.

In one embodiment of the method, the feedstream of step (b) is directed, before step (c), through at least one secondary drying chamber in fluid communication with the discharge outlet of the primary drying chamber to evaporate a second portion of the solvent into the drying gas. In a preferred embodiment, the secondary drying chamber comprises tubing having an inlet in fluid communication with the discharge outlet of the primary drying chamber, wherein the ratio of the cross-sectional area of the primary drying chamber to the cross-sectional area of the tubing is at least 4:3, and wherein the ratio of the length of the tubing to the length of the primary drying chamber is at least 2:1.

In another embodiment of the method, multiple nozzles are used in step (a) to introduce multiple emulsions, solutions, suspensions, or combinations thereof.

In one embodiment, the bulk material comprises a pharmaceutical agent. The pharmaceutical agent may be a therapeutic, a prophylactic, or a diagnostic agent. In one embodiment, the therapeutic or prophylactic agent comprises a hydrophobic drug and the particles are microspheres having voids or pores therein. In another embodiment, the bulk material comprises a diagnostic agent, such as an ultrasound contrast agent or another agent for diagnostic imaging. In another embodiment, the bulk material further comprises a shell forming material, such as a polymer (e.g., a biocompatible synthetic polymer), a lipid, a sugar, a protein, an amino acid, or a combination thereof.

In a preferred embodiment, the particles are microparticles. In one embodiment, the microparticles comprise microspheres having voids or pores therein.

In one embodiment, the bulk material comprises a therapeutic or prophylactic agent. In one embodiment, the therapeutic or prophylactic agent comprises a hydrophobic drug and the particles are microspheres having voids or pores therein. In another embodiment, the bulk material comprises a diagnostic agent, such as an ultrasound contrast agent or other agent for diagnostic imaging.

In one embodiment, the method further comprises adding an excipient material or pharmaceutical agent to the feedstream of step (b). For example, this could be done after the feedstream has flowed through a particle concentration means to separate and remove at least a portion of the drying gas from the feedstream. In another example, this could be done before the feedstream has flowed through a particle concentration means to separate and remove at least a portion of the drying gas from the feedstream. In a preferred embodiment, the excipient or pharmaceutical agent is in the form of a dry powder. Examples of the excipient material include amino acids, proteins, polymers, carbohydrates, starches, surfactants, and combinations thereof.

In another aspect, a method is provided for making a dry powder blend. The method includes the steps of (a) spraying an emulsion, solution, or suspension, which comprises a solvent and a bulk material, through an atomizer and into a primary drying chamber having a drying gas inlet, a discharge outlet, and a drying gas flowing therethrough, to form droplets comprising the solvent and the bulk material, wherein the droplets are dispersed in the drying gas; (b) evaporating, in the primary drying chamber, at least a portion of the solvent into the drying gas to solidify the droplets and form particles dispersed in the drying gas, the particles dispersed in the drying gas being a feedstream; (c) adding a dry powder excipient material to the feedstream to form a blended feedstream; and (d) flowing the particles and excipient material through a jet mill to deagglomerate or grind the particles and excipient material. Preferably, the method includes directing the feedstream of step (b) through a particle concentration means to separate and remove at least a portion of the drying gas from the feedstream. In one embodiment, the particles are microparticles comprising a pharmaceutical agent and the excipient material is in the form of microparticles having a size that is larger than the size of the microparticles comprising a pharmaceutical agent. In a preferred embodiment, step (d) is conducted to deagglomerate at least a portion of agglomerated particles, if any, while substantially maintaining the size and morphology of the individual particles. In another embodiment, a second pharmaceutical agent can be added in step (c), in place of or in addition to the excipient.

In another aspect, an apparatus is provided for making particles and deagglomerating or grinding them. In a preferred embodiment, the apparatus comprises: (a) an atomizer disposed for spraying an emulsion, solution, or suspension which comprises a solvent and a bulk material to form droplets of the solvent and the bulk material; (b) a primary drying chamber having a drying gas inlet and a discharge outlet, the atomizer being located in the primary drying chamber which provides for evaporation of at least a portion of the solvent into the drying gas to solidify the droplets and form particles dispersed in the drying gas; and (c) a jet mill having an inlet in fluid communication with the discharge outlet primary drying chamber, the jet mill being operable to receive the particles dispersed in at least a portion of the drying gas and grind or deagglomerate the particles.

In one embodiment, the apparatus further includes at least one secondary drying chamber interposed between, and in fluid communication with, the discharge outlet of the primary drying chamber and the inlet of the jet mill, which provides additional drying of the particles, i.e., provides for evaporation of a second portion of the solvent into the drying gas. In one version, the secondary drying chamber comprises tubing having an inlet in fluid communication with the discharge outlet of the primary drying chamber, wherein the ratio of the cross-sectional area of the primary drying chamber to the cross-sectional area of the tubing is at least 4:3, and wherein the ratio of the length of the tubing to the length of the primary drying chamber is at least 2:1.

In one embodiment, the apparatus also includes a particle concentration means, such as a cyclone separator, to separate and remove at least a portion of the drying gas from the particles, wherein the particle concentration means has a particle discharge outlet in fluid communication with the inlet of the jet mill.

In another embodiment, the apparatus further comprises a collection cyclone to separate the drying gas from the deagglomerated or ground particles that are discharged from the jet mill. Optionally, the apparatus includes a control valve to control the flow rate of the drying gas discharged from the collection cyclone, a control valve to control the flow rate of the drying gas discharged from the particle concentration means, or both of these control valves.

In one embodiment, the apparatus further comprises a means for introducing an excipient material into the particles and drying gas flowing between the discharge outlet of the primary drying chamber and the inlet of the jet mill. This apparatus can be used, for example, to make a dry powder blend in a single step, i.e., without intermediate collection and blending steps between spray drying and jet milling.

In one embodiment, the apparatus further comprises multiple nozzles to introduce separate emulsions, solutions, suspensions, or combinations thereof into the primary drying chamber. The multiple nozzles of this apparatus can be used, for example, to introduce materials that comprise a pharmaceutical agent, an excipient, or combinations thereof. The multiple nozzles can be used, for example, to spray the same material in order to increase the throughput or can be used to spray different materials in order to create dry powders that are mixtures of different particles.

In another aspect, pharmaceutical compositions are provided. These compositions comprise particles or dry powder blends made by the spray drying and in-line jet milling methods described herein.

DETAILED DESCRIPTION OF THE INVENTION

Process systems and methods have been developed for making particles, such as microparticles, by spray drying and then deagglomerating or grinding the particles using an in-line jet mill. By coupling spray drying with "in-line" jet milling, a single step process is created from two separate unit operations, and an additional collection step is eliminated, which otherwise would be associated with a yield loss and possible aseptic transfer which would be undesirable for pharmaceutical production. The one-step, in-line process has further advantages in time and cost of processing. In an optional embodiment, the systems also provide in-line blending of an excipient material with the particles.

The jet milling step beneficially lowers residual moisture and solvent levels in the particles, leading to better stability and handling properties for dry powder pharmaceutical formulations or other dry powder forms comprising the particles.

As used herein, the term "in-line" refers to process equipment in fluid communication arranged and adapted to process the materials in a continuous, sequential manner. That is, the particles being processed flow between and through the individual pieces of equipment, without an intervening collection step.

In a preferred embodiment the particles are microparticles.

In a preferred method, the microparticles comprise one or more pharmaceutical agents. In one embodiment, the microparticle is formed entirely of a pharmaceutical agent. In another embodiment, the microparticle has a core of pharmaceutical agent encapsulated in a shell. In yet another embodiment, the pharmaceutical agent is interspersed within the shell or matrix. In another embodiment, the pharmaceutical agent is uniformly mixed within the material comprising the shell or matrix. Optionally, the microparticles of any of these embodiments can be blended with one or more excipients.

I. In-Line Methods and Apparatus for Making Particles

The methods include (a) spraying an emulsion, solution, or suspension, which comprises a solvent and a bulk material, through one or more atomizers and into a primary drying chamber having a drying gas inlet, a discharge outlet, and a drying gas flowing therethrough, to form droplets comprising the solvent and the bulk material, wherein the droplets are dispersed in the drying gas; (b) evaporating, in the primary drying chamber, at least a portion of the solvent into the drying gas to solidify the droplets and form particles dispersed in the drying gas, the particles dispersed in the drying gas being a feedstream; and (c) flowing the particles and at least a portion of the drying gas of the feedstream through a jet mill to deagglomerate or grind the particles. In a preferred embodiment, step (c) is conducted to deagglomerate at least a portion of agglomerated particles, if any, while substantially maintaining the size and morphology of the individual particles. Alternatively, step (c) is conducted to grind the particles.

In a preferred embodiment, the feedstream of step (b) is directed through a particle concentration means to separate and remove at least a portion of the drying gas from the feedstream. This provides a concentration of solids in the dispersion entering the jet mill that is high enough to permit the jet mill to operate effectively as intended, i.e., to deagglomerate or grind the particles.

In another preferred embodiment, which can be used with or without the particle concentration means, the apparatus includes one or more secondary drying chambers interposed between, and in fluid communication with, the discharge outlet of the primary drying chamber and the inlet of the jet mill. These secondary drying chambers provide additional drying of the particles, that is, they provide time and volume for evaporation of a second portion of the solvent into the drying gas.

In yet another embodiment, which can be used with or without the particle concentration means and with or without the secondary drying chambers, the apparatus includes a means for introducing another material into the particles and drying gas flowing between the discharge outlet of the primary drying chamber and the inlet of the jet mill. In one embodiment, this other material could be an excipient, a second pharmaceutical agent, or a combination thereof. For example, a dry powder beta agonist could be introduced into a feed stream from a spray dryer that is producing microparticles containing a corticosteroid. This apparatus can be used, for example, to make a dry powder blend in a single step, i.e., without an intermediate collection step between spray drying and jet milling.

Figure 1:
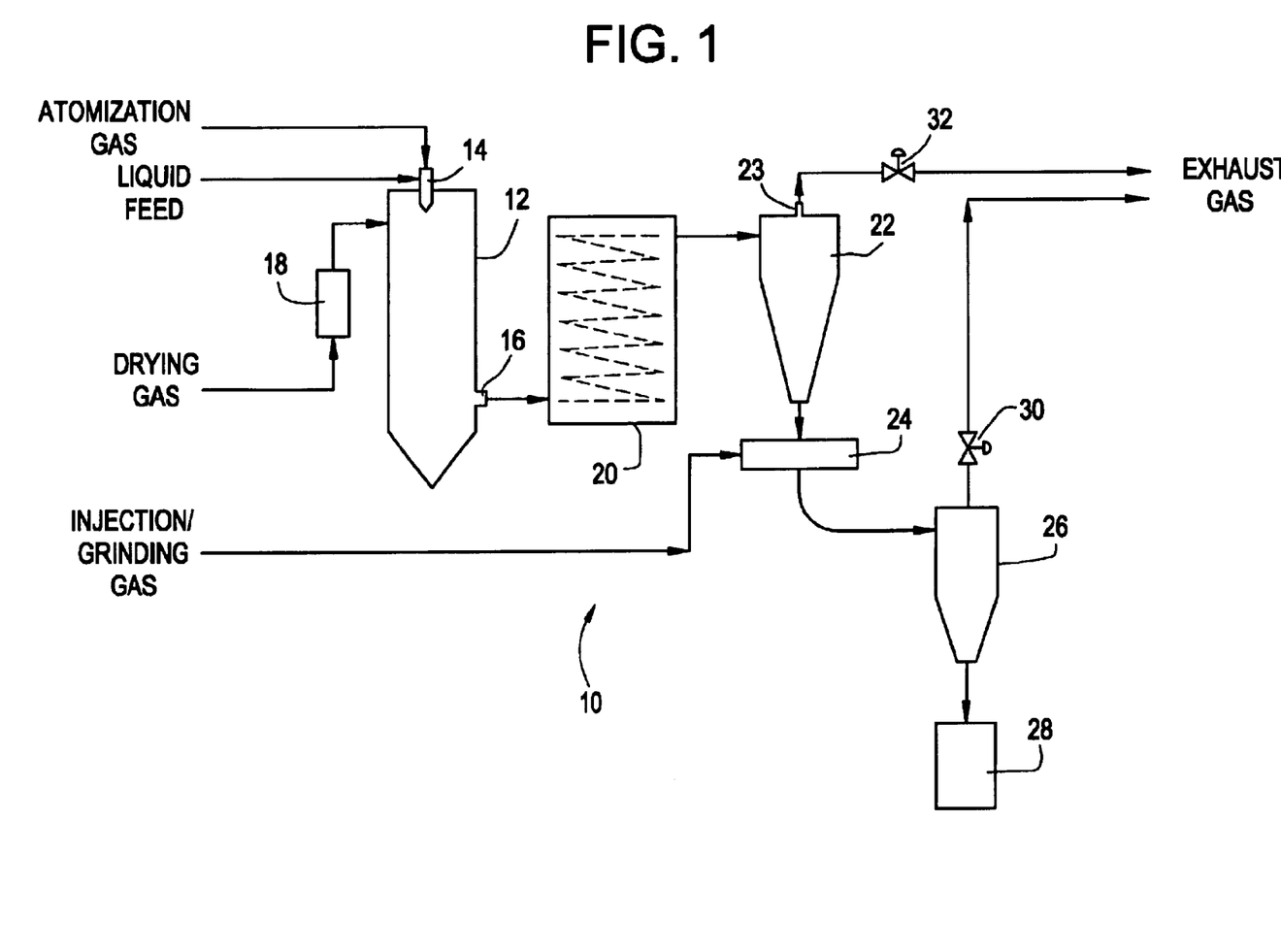
FIG. 1 is a process flow diagram of one embodiment of a process for making microparticles by spraying drying with in-line jet milling to deagglomerate or grind the microparticles.

FIG. 1 illustrates one example of an in-line system, or apparatus, 10 for making and jet-milling particles. A liquid feed (i.e., an emulsion, solution, or suspension, which comprises a solvent and a bulk material) and an atomization gas (e.g., air, nitrogen, etc.) are fed through an atomizer 14. The atomized droplets of solvent and bulk material are formed in the primary drying chamber 12. A drying gas is fed through an optional heater 18 and into a primary drying chamber 12. In the primary drying chamber, the droplets are dispersed in the drying gas, and at least a portion of the solvent is evaporated into the drying gas to solidify the droplets and form a feed a feedstream of particles dispersed in the drying gas. This feedstream then exits the primary drying chamber 12 through outlet 16 and enters (optional) secondary drying apparatus 20, which includes a coiled tube through which the feedstream flows. Upon exiting the secondary drying apparatus 20, the dispersion enters the cyclone separator 22, which serves to concentrate the particles. A portion of the drying gas is separated from the feedstream and exits the top vent 23 of the cyclone separator 22. The concentrated particles/drying gas then exits the cyclone separator 22 and flows into a jet mill 24. A grinding gas (e.g., dry nitrogen) also is supplied to the jet mill 24. The jet mill 24 deagglomerates or grinds the particles, depending, in part, on the operating parameters selected for the jet mill. The jet-milled particles dispersed in drying gas (and grinding gas) then flow from the jet mill 24 to a collection cyclone 26. The jet-milled particles are collected in collection jar 28 or other suitable apparatus, and the drying and grinding gases are exhausted from the system 10. The exhaust gas from the cyclones 22 and 26 typically is filtered (filters not shown) before release from the system and/or into the atmosphere.

Figure 2:
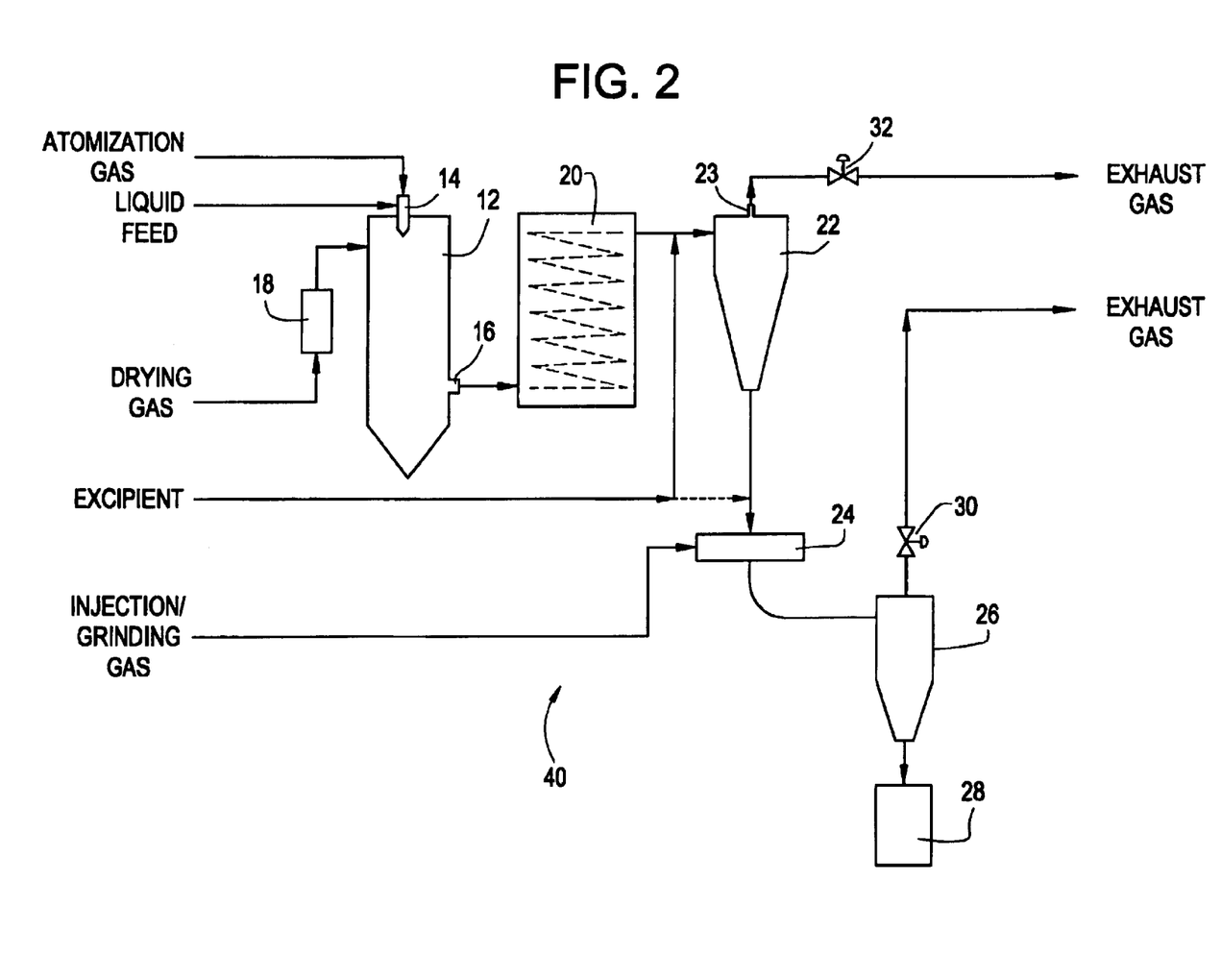
FIG. 2 is a process flow diagram of one embodiment of a process for making blends of microparticles by spray drying with in-line excipient feeding and in-line jet milling.
Figure 3:
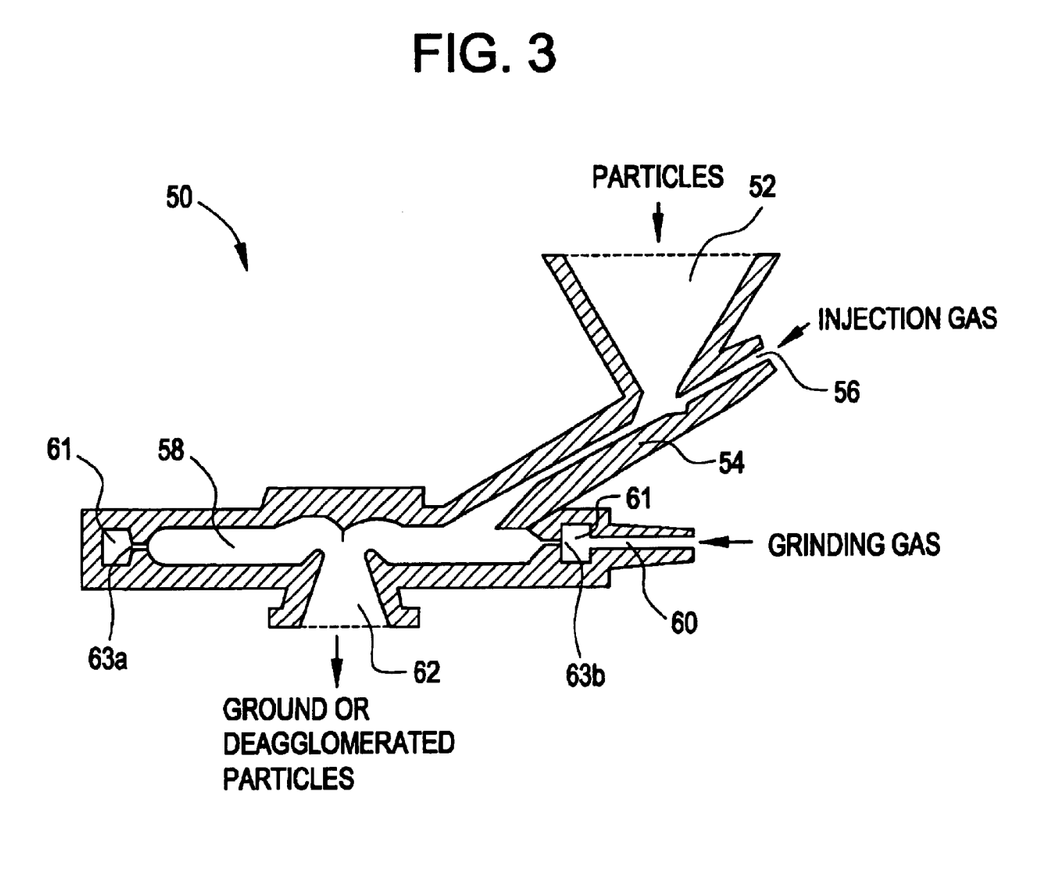
FIG. 3 is a cross-sectional view of a typical jet mill that can be incorporated into the in-line process for spray drying and jet milling.

FIG. 2 illustrates one example of an in-line system, or apparatus, 40 for making particle blends. In the embodiment shown, particles are made by spray drying, directly blended with an excipient using an in-line excipient feed device, and then the resulting blend is jet-milled using an in-line jet mill, to yield a highly uniform particle blend. The process is like that shown in FIG. 1, except an excipient material (or pharmaceutical material or combination thereof) is added to the particles/drying gas, after, or more preferably before, the particles/drying gas flows through cyclone separator 22. The resulting mixture of particles, excipient material, and drying gas then flows into jet mill 24, where the mixture is deagglomerated or ground. The jet-milled particle/excipient blend dispersed in drying gas then flows from the jet mill 24 to a collection cyclone 26 and collected in collection jar 28. The drying gas and grinding gas are exhausted from system 40, as described above.

Preferably, the methods and systems are adapted for making pharmaceutical formulations comprising microparticles. The microparticles are made by spray drying, and the jet milling is effective to deagglomerate or grind the microparticles. The jet-milling step can advantageously reduce moisture content and residual solvent levels in the formulation through the addition of dry and solvent free gas directly to the jet mill (e.g., as grinding gas). The jet-milling step also can improve the suspendability and wettability of the dry powder formulation (e.g., for better injectability) and give the dry powder formulation improved aerodynamic properties (e.g., for better pulmonary delivery).

The use of a of a spray dryer with an in-line jet mill, as opposed to a two-step process of a spray drying followed by a separate jet milling process, advantageously improves yield, reduces time, and reduces cost.

Spray Drying

The particles are formed by a spray drying technique known in the art. For example, the particles can be produced using the spray drying methods and devices described, for example, in U.S. Pat. No. 5,853,698 to Straub et al., U.S. Pat. No. 5,611,344 to Bernstein et al., U.S. Pat. No. 6,395,300 to Straub et al., and U.S. Pat. No. 6,223,455 to Chickering III, et al., which are incorporated herein by reference.

As used herein (in the examples), the symbol "Ø" is used to indicate the term "diameter" for the object being described.

As used herein, the term "solvent" refers to the liquid in which the material forming the bulk of the spray dried particle is dissolved, suspended, or emulsified for delivery to the atomizer of a spray dryer and which is evaporated into the drying gas, whether or not the liquid is a solvent or nonsolvent for the material. Other volatilizable components, such as a volatile salt, may be included in the bulk material/liquid, and volatilized into the drying gas.

In one embodiment, microparticles are produced by dissolving a pharmaceutical agent and/or shell material in an appropriate solvent, (and optionally dispersing a solid or liquid active agent, pore forming agent (e.g., a volatile salt), or other additive into the solution containing the pharmaceutical agent and/or shell material) and then spray drying the solution, to form microparticles. As defined herein, the process of "spray drying" a solution containing a pharmaceutical agent and/or shell material refers to a process wherein the solution is atomized to form a mist and dried by direct contact with carrier gases. Using spray drying equipment available in the art, the solution containing the pharmaceutical agent and/or shell material may be atomized into a drying chamber, dried within the chamber, and then collected via a cyclone at the outlet of the chamber. Representative examples of types of suitable atomization devices include ultrasonic, pressure feed, air atomizing, and rotating disk. The temperature may be varied depending on the solvent or materials used. The temperature of the inlet and outlet ports can be controlled to produce the desired products. Multiple nozzles (or other atomization devices) can be used to allow for introduction of multiple emulsions, solutions, suspensions, or combinations thereof into the primary drying chamber. The multiple nozzles can be used, for example, to introduce materials that comprise a pharmaceutical agent, an excipient, or combinations thereof. In one embodiment, the multiple nozzles are used to spray the same material (from each nozzle) in order increase process throughput of the material. In another embodiment, the multiple nozzles are used to spray different materials (e.g., different materials from each nozzle), for example, in order to create dry powders that are mixtures of different particles, e.g., composed of different materials.

The size of the particulates of pharmaceutical agent and/or shell material is a function of the nozzle used to spray the solution of the pharmaceutical agent and/or shell material, nozzle pressure, the solution and atomization flow rates, the pharmaceutical agent and/or shell material used, the concentration of the pharmaceutical agent and/or shell material, the type of solvent, the temperature of spraying (both inlet and outlet temperature), and the molecular weight of a shell material such as a polymer or other matrix material. Generally, if a polymer is used the higher the molecular weight, the larger the particle size, assuming the concentration is the same (because an increase in molecular weight generally increases the solution viscosity). Particles having a target diameter between 0.5 $\mu$m and 500 $\mu$m can be obtained. The morphology of these microparticles depends, for example, on the selection of shell material, concentration, molecular weight of a shell material such as a polymer or other matrix material, spray flow, and drying conditions.

In an optional embodiment, the apparatus further includes one or more secondary drying chambers downstream from the primary drying chamber to provide additional solvent removal. In one embodiment, the secondary drying chamber comprises the drying apparatus described in U.S. Pat. No. 6,308,434 and U.S. Pat. No. 6,223,455, which are hereby incorporated by reference. The secondary drying chamber preferably comprises tubing having an inlet in fluid communication with the discharge outlet of the primary drying chamber, to evaporate a second portion of the solvent into the drying gas, wherein the ratio of the cross-sectional area of the primary drying chamber to the cross-sectional area of the tubing is at least 4:3, and wherein the ratio of the length of the tubing to the length of the primary drying chamber is at least 2:1.

Particle Concentration Means and Process Control

The particle concentration means can be essentially any device suitable for concentrating the particles in the drying gas such that the particles can be effectively jet milled, whether for grinding or deagglomeration. Representative devices for concentrating the particles in the drying gas include cyclone separators, gravity settling chambers (knock-out pots), electrostatic charge precipitators, impingement separators, mechanical centrifugal separators and uniflow cyclones.

In a preferred embodiment, the particle concentration means includes at least one cyclone separator as known in the art, to separate and remove at least a portion of the drying gas from said particles. In a typical embodiment, the cyclone separator consists of a vertical cylinder with a conical bottom. The particle/drying gas dispersion enters the cyclone through a tangential inlet near the top, entering in a vertical motion. The centrifugal force created causes the particles to be thrown toward the wall, and the drying gas falls downward along the wall and then spirals upward through the center when it reaches the bottom, producing a double vortex. The particles fall by gravity to the bottom of the device. One skilled in the art can select the appropriate dimensions of the separator based, for example, on the flow rates of gas and particles, percentage of gas to be separated, system pressures, particle mass and size, etc.

For a particular system, successful operation requires balancing of the flows and pressures in the process equipment, such that jet mill performance is maximized, particle blowback from the jet mill is avoided, and clogging of the cyclone and/or jet mill is avoided. For example, as shown in FIG. 1 and FIG. 2, control of the flow through the system 10 or system 40 can be performed with the use of a control valve 30 downstream from the collection cyclone 26 and/or a control valve 32 downstream from the separator cyclone 22, either or both of which can be used to control the pressure on the systems. For example, by increasing the backpressure on the system, more drying gas can be separated and expelled through the top vent of the cyclone separator. Alternatively, less drying gas can be directed through the top vent of the cyclone separator by lowering the backpressure on the system. Alternatively, the drying gas exhausted through the cyclone separator can be in part or entirely redirected into the system downstream of the jet mill outlet. Optionally, fresh gas can be added into the system downstream of the jet mill outlet. Such redirected or added gases can be used to balance pressures in the process.

While a control valve is shown in FIGS. 1 and 2, other flow controlling devices known in the art can be used to control the system pressure and/or flow rate of drying gas discharged from the particle concentration means or the collection cyclone. For example, the flow controlling devices could comprise a device selected from control valves, filters, regulators, orifices, and combinations thereof.

In one embodiment, the solids content of the feedstream (particles/drying gas) from the primary and secondary drying chambers is increased by separating out between about 50 and 100 vol.%, more preferably about 90 and 100 vol.%, of the drying gas, which is expelled through top vent 23. For example, in one embodiment, the flow rate of the particles/drying gas from the spray dryer is 52 CFM (1500 L/min.) and the flow rate of the particles/drying gas to the jet mill is 0.52 CFM (15 L/min.). The system components would be sized to maintain the appropriate gas velocity throughout the process.

Jet Milling

As used herein, the terms "jet mill" and "jet milling" include and refer to the use of any type of fluid energy impact mills, including, but not limited to, spiral jet mills, loop jet mills, hammer mills, grinders, crushers, and fluidized bed jet mills, with or without internal air classifiers. These mills are known in the art. The jet mill is used to deagglomerate or to grind the particles.

As used herein, the term "deagglomerate" refers to the technique for substantially deagglomerating microparticle agglomerates that have been produced during or subsequent to formation of the microparticles, by bombarding the feed particles with high velocity air or other gas, typically in a spiral or circular flow. The jet milling process conditions can be selected so that the microparticles are substantially deagglomerated while substantially maintaining the size and morphology of the individual microparticles, which can be quantified as providing a volume average size reduction of at least 15% and a number average size reduction of no more than 75%.

As used herein, the terms "grind", "ground", or "grinding" refers to particle size reduction by fracture, e.g., conventional milling. That is, the particles and/or agglomerates are reduced in size without substantially maintaining the size and morphology of the individual microparticles. The process is characterized by the acceleration of particles in a gas stream to high velocities for impingement on other particles, similarly accelerated, or impingement on the walls of the mill.

A typical spiral jet mill 50 is illustrated in FIG. 3. Particles, with or without drying gas, are fed into feed chute 52. Optional injection gas is fed through one or more ports 56. The particles are forced through injector 54 into chamber 58. The particles enter an extremely rapid vortex in the chamber 58, where they collide with one another until small enough to become sufficiently entrained in the gas stream to exit a central discharge port 62 in the jet mill by the gas stream (against centrifugal forces experienced in the vortex). Grinding gas (so-named whether the jet mill is used for grinding or deagglomeration) is fed from port 60 into gas supply ring 61. The grinding gas then is fed into the chamber 58 via a plurality of apertures; only two 63*a* and 63*b* are shown. Ground or deagglomerated particles are discharged from the jet mill 50.

The selection of the material forming the bulk of the particles and the temperature of the particles in the jet mill are among the factors that affect deagglomeration and grinding. Therefore, the jet mill optionally can be provided with a temperature control system. For example, the control system may heat the particles, rendering the material less brittle and thus less easily fractured in the jet mill, thereby minimizing unwanted size reduction. Alternatively, the control system may need to cool the particles to below the glass transition or melting temperature of the material, so that deagglomeration is possible.

In a preferred embodiment, the particles are aseptically fed to the jet mill, and a suitable gas, preferably dry nitrogen, is used to process the microparticles through the mill. Grinding and injection gas pressures can be adjusted as need, for example, based on the material characteristics. Preferably, these gas pressures are between 0 and 10 bar, more preferably between 2 and 8 bar. Particle throughput depends on the size and capacity of the jet mill. The jet-milled particles can be collected by filtration or, more preferably, cyclone.

Jet milling the particles, in addition to providing the desired level of deagglomeration or grinding, can also lower the residual solvent and moisture levels in the particles or particle blend while in process (i.e., before collection), due to the addition of dry and solvent free gas (e.g., as grinding gas, injection gas, or both) provided to the jet mill. To achieve reduced residual levels, the injection/grinding gas preferably is a low humidity gas, such as dry nitrogen. In one embodiment, the injection/grinding gas is at a temperature less than 100° C. (e.g., less than 75° C., less than 50° C., less than 25° C., etc.).

Blending

In an optional embodiment, the process further includes blending the particles with another material (e.g., an excipient material, a (second) pharmaceutical agent, or a combination thereof), which can be in a dry powder form. The blending can be performed before jet milling as an in-line process, after jet milling, or both before and after jet milling.

In a preferred embodiment, the blending is conducted in a single step process, such as an in-line process, as shown for example in FIG. 2. This process comprises spray drying with in-line blending and in-line jet milling. The excipient material preferably is added to the feedstream before it flows into the jet mill. The excipient material can be introduced into the feedstream using essentially any suitable introduction means known in the art. Non-limiting examples of such introduction means include screw or vibratory feed from a closed hopper, a venturi feed from a vented hopper, via a feedstream from one or more other spray drying units making the excipient particles, or via a feedstream from one or more jet milling devices. One skilled in the art can readily connect a feed source line using standard techniques and provide the excipient feed material at a sufficient pressure to cause the material to flow into and combine with the drying gas and particles.

In another embodiment, the excipient material is blended with the particles post-jet milling, in a batch or continuous process, including an in-line process. The blending can be carried out using essentially any technique or device suitable for combining the microparticles with one or more other materials (e.g., excipients), preferably to achieve uniformity of blend.

Content uniformity of solid-solid pharmaceutical blends is critical. Jet milling can be conducted on the microparticles before blending or as part of a single process (spray drying with in-line blending and in-line jet milling) to enhance content uniformity. Jet-milling advantageously can provide improved wetting and dispersibility upon reconstitution of the blends. In addition, the resulting microparticle formulation can provide improved injectability, passing through the needle of a syringe more easily. Jet milling can provide improved dispersibility of the dry powder, which provides for improved aerodynamic properties for nasal or pulmonary administration.

Other Steps in the Process

The particles may undergo additional processing steps. Representative examples of such processes include lyophilization or vacuum drying to further remove residual solvents, temperature conditioning to anneal materials, size classification to recover or remove certain fractions of the particles (i.e., to optimize the size distribution), compression molding to form a tablet or other geometry, and packaging. In one embodiment, oversized (e.g., 20 μm or larger, preferably 10 μm or larger) microparticles are separated from the microparticles of interest. Some formulations also may undergo sterilization, such as by gamma irradiation.

II. The Particles

The particles made by the processes described herein comprise a bulk material. As used herein, the term "bulk material" includes essentially any material that can be provided in a solution, suspension, or emulsion, and then fed through an atomizer and dried to form particles. In preferred embodiments, the bulk material is a pharmaceutical agent, a shell material, or a combination of a pharmaceutical agent and a shell material, as described herein.

Size and Morphology

The particles made by the in-line spray drying and jet mill process can be of any size. As used herein, the term "particle" includes micro-, submicro-, and macro-particles. Generally, the particles are between about 100 nm and 5 mm in diameter or in the longest dimension. In a preferred embodiment, the particles are microparticles, which are between 1 and 999 microns in diameter or in the longest dimension. As used herein, the term "microparticle" includes microspheres and microcapsules, as well as microparticles, unless otherwise specified. Microparticles may or may not be spherical in shape. Microcapsules are defined as microparticles having an outer shell surrounding a core of another material, such as a pharmaceutical agent. The core can be gas, liquid, gel, or solid. Microspheres can be solid spheres or can be porous and include a sponge-like or honeycomb structure formed by pores or voids in a matrix material or shell.

As used herein, the terms "size" or "diameter" in reference to particles refers to the number average particle size, unless otherwise specified. An example of an equation that can be used to describe the number average particle size is shown below:

$$\frac{\sum_{i=1}^{p} n_i d_i}{\sum_{i=1}^{p} n_i}$$

where n=number of particles of a given diameter (d).

As used herein, the term "volume average diameter" refers to the volume weighted diameter average. An example of equations that can be used to describe the volume average diameter is shown below:

$$\left[\frac{\sum_{i=1}^{p} n_i d_i^3}{\sum_{i=1}^{p} n_i}\right]^{1/3}$$

where n=number of particles of a given diameter (d).

As used herein, the term "aerodynamic diameter" refers to the equivalent diameter of a sphere with density of 1 g/mL were it to fall under gravity with the same velocity as the particle analyzed. Aerodynamic diameters can be determined on the dry powder using an Aerosizer (TSI), which is a time of flight technique, or by cascade impaction or liquid impinger techniques.

Particle size analysis can be performed on a Coulter counter, by light microscopy, scanning electron microscopy, transmittance electron microscopy, laser diffraction methods such as those using a Malvern Mastersizer, light scattering methods or time of flight methods. Where a Coulter method is described, the powder is dispersed in an electrolyte, and the resulting suspension analyzed using a Coulter Multisizer II fitted with a 50-μm aperture tube.

In one embodiment, the jet milling process described herein can deagglomerate agglomerated particles, such that the size and morphology of the individual particles is substantially maintained. That is, a comparison of the particle size before and after jet milling should show a volume average size reduction of at least 15% and a number average size reduction of no more than 75%. It is believed that the jet milling processes will be most useful in deagglomerating particles having a volume average diameter or aerodynamic average diameter greater than about 2 μm.

In one embodiment, the particles are microparticles comprising a pharmaceutical agent for use in a pharmaceutical formulation. These microparticles preferably have a number average size between about 1 and 10 μm. In one embodiment, the microparticles have a volume average size between 2 and 50 μm. In another embodiment, the microparticles have an aerodynamic diameter between 1 and 50 μm.

The pharmaceutical agent containing particles typically are manufactured to have a size (i.e., diameter) suitable for the intended route of administration. Particle size also can affect RES uptake. For intravascular administration, the particles preferably have a diameter of between 0.5 and 8 μm. For subcutaneous or intramuscular administration, the particles preferably have a diameter of between about 1 and 100 μm. For oral administration for delivery to the gastrointestinal tract and for application to other lumens or mucosal surfaces (e.g., rectal, vaginal, buccal, or nasal), the particles preferably have a diameter of between 0.5 μm and 5 mm. A preferred size for administration to the pulmonary system is an aerodynamic diameter of between 1 and 5 μm, with an actual volume average diameter (or an aerodynamic average diameter) of 5 μm or less.

In one embodiment, the particles comprise microparticles having voids therein.

In one embodiment, the microparticles have a number average size between 1 and 3 μm and a volume average size between 3 and 8 μm.

Pharmaceutical Agents

The pharmaceutical agent is a therapeutic, diagnostic, or prophylactic agent. The pharmaceutical agent is sometimes referred to herein generally as a "drug" or "active agent." The pharmaceutical agent in the final powder may be present in an amorphous state, a crystalline state, or a mixture thereof.

A wide variety of drugs can be loaded into the microparticles. These can be small molecules, proteins or peptides, carbohydrates, oligosaccharides, nucleic acid molecules, or other synthetic or natural agents. Examples of suitable drugs include the classes and species of drugs described in Martindale, *The Extra Pharmacopoeia*, 30th Ed. (The Pharmaceutical Press, London 1993). The drug can be in any suitable form, including various salt forms, free acid forms, free base forms, and hydrates.

In one embodiment, the pharmaceutical agent is a contrast agent for diagnostic imaging. For example, the agent could be a gas for ultrasound imaging, as described for example in U.S. Pat. No. 5,611,344 to Bernstein et al., which is incorporated herein by reference. Other examples of suitable diagnostic agents useful herein include those agents known in the art for use in positron emission tomography (PET), computer assisted tomography (CAT), single photon emission computerized tomography, x-ray, fluoroscopy, and magnetic resonance imaging (MRI).

In other embodiments, the pharmaceutical agent is a therapeutic or prophylactic agent. Non-limiting examples of these agents include water soluble drugs, such as ceftriaxone, ketoconazole, ceftazidime, oxaprozin, albuterol, valacyclovir, urofollitropin, famciclovir, flutamide, enalapril, mefformin, itraconazole, buspirone, gabapentin, fosinopril, tramadol, acarbose, lorazepan, follitropin, glipizide, omeprazole, fluoxetine, lisinopril, tramsdol, levofloxacin, zafirlukast, interferon, growth hormone, interleukin, erythropoietin, granulocyte stimulating factor, nizatidine, bupropion, perindopril, erbumine, adenosine, alendronate, alprostadil, benazepril, betaxolol, bleomycin sulfate, dexfenfluramine, diltiazem, fentanyl, flecainid, gemcitabine, glatiramer acetate, granisetron, lamivudine, mangafodipir trisodium, mesalamine, metoprolol fumarate, metronidazole, miglitol, moexipril, monteleukast, octreotide acetate, olopatadine, paricalcitol, somatropin, sumatriptan succinate, tacrine, verapamil, nabumetone, trovafloxacin, dolasetron, zidovudine, finasteride, tobramycin, isradipine, tolcapone, enoxaparin, fluconazole, lansoprazole, terbinafine, pamidronate, didanosine, diclofenac, cisapride, venlafaxine, troglitazone, fluvastatin, losartan, imiglucerase, donepezil, olanzapine, valsartan, fexofenadine, calcitonin, or ipratropium bromide.

Other examples include hydrophobic drugs such as celecoxib, rofecoxib, paclitaxel, docetaxel, acyclovir, alprazolam, amiodaron, amoxicillin, anagrelide, aripiprazole, bactrim, biaxin, budesonide, bulsulfan, carbamazepine, ceftazidime, cefprozil, ciprofloxicin, clarithromycin, clozapine, cyclosporine, diazepam, estradiol, etodolac, famciclovir, fenofibrate, fexofenadine, gemcitabine, ganciclovir, itraconazole, lamotrigine, loratidine, lorazepam, meloxicam, mesalamine, minocycline, modafinil, nabumetone, nelfinavir mesylate, olanzapine, oxcarbazepine, phenytoin, propofol, ritinavir, risperidone, SN-38, sulfamethoxazol, sulfasalazine, tacrolimus, tiagabine, tizanidine, trimethoprim, valium, valsartan, voriconazole, zafirlukast, zileuton, and ziprasidone. In this embodiment, the particles made by the processes described herein preferably are porous.

In one embodiment, the pharmaceutical agent is for pulmonary administration. Non-limiting examples include corticosteroids such as budesonide, fluticasone propionate, beclomethasone dipropionate, mometasone, flunisolide, and triamcinolone acetonide; other steroids such as testosterone, progesterone, and estradiol; leukotriene inhibitors such as zafirlukast and zileuton; antibiotics such as cefprozil, amoxicillin; antifungals such as ciprofloxacin, and itraconazole; bronchiodilators such as albuterol, formoterol and salmeterol; antineoplastics such as paclitaxel and docetaxel; and peptides or proteins such as insulin, calcitonin, leuprolide, granulocyte colony-stimulating factor, parathyroid hormone-related peptide, and somatostatin.

Examples of preferred drugs include aripirazole, risperidone, albuterol, adapalene, doxazosin mesylate, mometasone furoate, ursodiol, amphotericin, enalapril maleate, felodipine, nefazodone hydrochloride, valrubicin, albendazole, conjugated estrogens, medroxyprogesterone acetate, nicardipine hydrochloride, zolpidem tartrate, amlodipine besylate, ethinyl estradiol, omeprazole, rubitecan, amlodipine besylate/ benazepril hydrochloride, etodolac, paroxetine hydrochloride, paclitaxel, atovaquone, felodipine, podofilox, paricalcitol, betamethasone dipropionate, fentanyl, pramipexole dihydrochloride, Vitamin $D_3$ and related analogues, finasteride, quetiapine fumarate, alprostadil, candesartan, cilexetil, fluconazole, ritonavir, busulfan, carbamazepine, flumazenil, risperidone, carbemazepine, carbidopa, levodopa, ganciclovir, saquinavir, amprenavir, carboplatin, glyburide, sertraline hydrochloride, rofecoxib carvedilol, halobetasolproprionate, sildenafil citrate, celecoxib, chlorthalidone, imiquimod, simvastatin, citalopram, ciprofloxacin, irinotecan hydrochloride, sparfloxacin, efavirenz, cisapride monohydrate, lansoprazole, tamsulosin hydrochloride, mofafinil, clarithromycin, letrozole, terbinafine hydrochloride, rosiglitazone maleate, diclofenac sodium, lomefloxacin hydrochloride, tirofiban hydrochloride, telmisartan, diazapam, loratadine, toremifene citrate, thalidomide, dinoprostone, mefloquine hydrochloride, trandolapril, docetaxel, mitoxantrone hydrochloride, tretinoin, etodolac, triamcinolone acetate, estradiol, ursodiol, nelfinavir mesylate, indinavir, beclomethasone dipropionate, oxaprozin, flutamide, famotidine, nifedipine, prednisone, cefuroxime, lorazepam, digoxin, lovastatin, griseofulvin, naproxen, ibuprofen, isotretinoin, tamoxifen citrate, nimodipine, amiodarone, budesonide, formoterol, flucasone propionate, salmeterol, and alprazolam.

Shell Material

The shell material can be a synthetic material or a natural material. The shell material can be water soluble or water insoluble. The particles can be formed of non-biodegradable or biodegradable materials, although biodegradable materials are preferred, particularly for parenteral administration. Examples of types of shell materials include, but are not limited to, polymers, amino acids, sugars, proteins, carbohydrates, and lipids. Polymeric shell materials can be degradable or non-degradable, erodible or non-erodible, natural or synthetic. Non-erodible polymers may be used for oral administration. In general, synthetic polymers are preferred due to more reproducible synthesis and degradation. Natural polymers also may be used. Natural biopolymers that degrade by hydrolysis, such as polyhydroxybutyrate, may be of particular interest. The polymer is selected based on a variety of performance factors, including the time required for in vivo stability, i.e., the time required for distribution to the site where delivery is desired, and the time desired for delivery. Other selection factors may include shelf life, degradation rate, mechanical properties, and glass transition temperature of the polymer.

Representative synthetic polymers are poly(hydroxy acids) such as poly(lactic acid), poly(glycolic acid), and poly(lactic acid-co-glycolic acid), poly(lactide), poly (glycolide), poly(lactide-co-glycolide), polyanhydrides, polyorthoesters, polyamides, polycarbonates, polyalkylenes such as polyethylene and polypropylene, polyalkylene glycols such as poly(ethylene glycol), polyalkylene oxides such as poly(ethylene oxide), polyalkylene terepthalates such as poly(ethylene terephthalate), polyvinyl alcohols, polyvinyl ethers, polyvinyl esters, polyvinyl halides such as poly(vinyl chloride), polyvinylpyrrolidone, polysiloxanes, poly(vinyl alcohols), poly(vinyl acetate), polystyrene, polyurethanes and co-polymers thereof, derivativized celluloses such as alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxyethyl cellulose, cellulose triacetate, and cellulose sulphate sodium salt jointly referred to herein as "synthetic celluloses"), polymers of acrylic acid, methacrylic acid or copolymers or derivatives thereof including esters, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate) Oointly referred to herein as "polyacrylic acids"), poly(butyric acid), poly(valeric acid), and poly(lactide-co-caprolactone), copolymers and blends thereof. As used herein, "derivatives" include polymers having substitutions, additions of chemical groups, for example, alkyl, alkylene, hydroxylations, oxidations, salt formations, and other modifications routinely made by those skilled in the art.

Examples of preferred biodegradable polymers include polymers of hydroxy acids such as lactic acid and glycolic acid, and copolymers with PEG, polyanhydrides, poly (ortho)esters, polyurethanes, poly(butyric acid), poly(valeric acid), poly(lactide-co-caprolactone), blends and copolymers thereof.

Examples of preferred natural polymers include proteins such as albumin and prolamines, for example, zein, and polysaccharides such as alginate, cellulose and polyhydroxyalkanoates, for example, polyhydroxybutyrate. The in vivo stability of the matrix can be adjusted during the production by using polymers such as polylactide-co-glycolide copolymerized with polyethylene glycol (PEG). PEG, if exposed on the external surface, may extend the time these materials circulate, as it is hydrophilic and has been demonstrated to mask RES (reticuloendothelial system) recognition.

Examples of preferred non-biodegradable polymers include ethylene vinyl acetate, poly(meth)acrylic acid, polyamides, copolymers and mixtures thereof.

Bioadhesive polymers of particular interest for use in targeting of mucosal surfaces include, but are not limited to, polyanhydrides, polyacrylic acid, poly(methyl methacrylates), poly(ethyl methacrylates), poly (butylmethacrylate), poly(isobutyl methacrylate), poly (hexylmethacrylate), poly(isodecyl methacrylate), poly (lauryl methacrylate), poly(phenyl methacrylate), poly (methyl acrylate), poly(isopropyl acrylate), poly(isobutyl acrylate), and poly(octadecyl acrylate).

Representative amino acids that can be used in the shell include both naturally occurring and non-naturally occurring amino acids. The amino acids can be hydrophobic or hydrophilic and may be D amino acids, L amino acids or racemic mixtures. Amino acids that can be used include, but are not limited to, glycine, arginine, histidine, threonine, asparagine, aspartic acid, serine, glutamate, proline, cysteine, methionine, valine, leucine, isoleucine, tryptophan, phenylalanine, tyrosine, lysine, alanine, and glutamine. The amino acid can be used as a bulking agent, or as an anti-crystallization agent for drugs in the amorphous state, or as a crystal growth inhibitor for drugs in the crystalline state or as a wetting agent. Hydrophobic amino acids such as leucine, isoleucine, alanine, glucine, valine, proline, cysteine, methionine, phenylalanine, tryptophan are more likely to be effective as anticrystallization agents or crystal growth inhibitors. In addition, amino acids can serve to make the shell have a pH dependency that can be used to influence the pharmaceutical properties of the shell such as solubility, rate of dissolution or wetting.

The shell material can be the same or different from the excipient material, if present. In one embodiment, the excipient can comprise the same classes or types of material used to form the shell. In another embodiment, the excipient comprises one or more materials different from the shell material. In this latter embodiment, the excipient can be a surfactant, wetting agent, salt, bulking agent, etc. In one embodiment, the formulation comprises (i) microparticles that have a core of a drug and a shell comprising a sugar or amino acid, blended with (ii) another sugar or amino acid that functions as a bulking or tonicity agent.

Excipients For particles to be used in pharmaceutical applications, the term "excipient" refers to any non-active ingredient of the formulation intended to facilitate delivery and administration by the intended route. For example, the excipient can comprise amino acids, sugars or other carbohydrates, starches, surfactants, proteins, lipids, or combinations thereof. The excipient may enhance handling, stability, aerodynamic properties and dispersibility of the active agent.

In preferred embodiments, the excipient is a dry powder (e.g., in the form of microparticles), which is blended with drug microparticles. Preferably, the excipient microparticles are larger in size than the pharmaceutical microparticles. In one embodiment, the excipient microparticles have a volume average size between about 10 and 1000 $\mu$m, preferably between 20 and 200 $\mu$m, more preferably between 40 and 100 $\mu$m.

Representative amino acids that can be used in the drug matrices include both naturally occurring and non-naturally occurring amino acids. The amino acids can be hydrophobic or hydrophilic and may be D amino acids, L amino acids or racemic mixtures. Non-limiting examples of amino acids that can be used include glycine, arginine, histidine, threonine, asparagine, aspartic acid, serine, glutamate, proline, cysteine, methionine, valine, leucine, isoleucine, tryptophan, phenylalanine, tyrosine, lysine, alanine, glutamine. The amino acid can be used as a bulking agent, or as a crystal growth inhibitor for drugs in the crystalline state or as a wetting agent. Hydrophobic amino acids such as leucine, isoleucine, alanine, glucine, valine, proline, cysteine, methionine, phenylalanine, tryptophan are more likely to be effective as crystal growth inhibitors. In addition, amino acids can serve to make the matrix have a pH dependency that can be used to influence the pharmaceutical properties of the matrix such as solubility, rate of dissolution, or wetting.

Examples of excipients include pharmaceutically acceptable carriers and bulking agents, including sugars such as lactose, mannitol, trehalose, xylitol, sorbitol, dextran, sucrose, and fructose. Other suitable excipients include surface active agents, dispersants, osmotic agents, binders, disintegrants, glidants, diluents, color agents, flavoring agents, sweeteners, and lubricants. Examples include sodium desoxycholate; sodium dodecylsulfate; polyoxyethylene sorbitan fatty acid esters, e.g., polyoxyethylene 20 sorbitan monolaurate (TWEEN™ 20), polyoxyethylene 4 sorbitan monolaurate (TWEEN™ 21), polyoxyethylene 20 sorbitan monopalmitate (TWEEN™ 40), polyoxyethylene 20 sorbitan monooleate (TWEEN™ 80); polyoxyethylene alkyl ethers, e.g., polyoxyethylene 4 lauryl ether (BRIJ™ 30), polyoxyethylene 23 lauryl ether (BRIJ™ 35), polyoxyethylene 10 oleyl ether (BRIJ™ 97); and polyoxyethylene glycol esters, e.g., poloxyethylene 8 stearate (MYRJ™ 45), poloxyethylene 40 stearate (MYRJ™ 52), Spans, Tyloxapol or mixtures thereof.

Examples of binders include starch, gelatin, sugars, gums, polyethylene glycol, ethylcellulose, waxes and polyvinylpyrrolidone. Examples of disintegrants (including super disintegrants) include starch, clay, celluloses, croscarmelose, crospovidone and sodium starch glycolate. Examples of glidants include colloidal silicon dioxide and talc. Examples of diluents include dicalcium phosphate, calcium sulfate, lactose, cellulose, kaolin, mannitol, sodium chloride, dry starch and powdered sugar. Examples of lubricants include talc, magnesium stearate, calcium stearate, stearic acid, hydrogenated vegetable oils, and polyethylene glycol.

The amounts of excipient for a particular formulation depend on a variety of factors and can be selected by one skilled in the art. Examples of these factors include the choice of excipient, the type and amount of drug, the microparticle size and morphology, and the desired properties and route of administration of the final formulation.

In one embodiment for injectable microparticles, a combination of mannitol and TWEEN™ 80 is blended with polymeric microspheres. In one case, the mannitol is provided at between 50 and 200% w/w, preferably 90 and 130% w/w, microparticles, while the TWEEN™ 80 is provided at between 0.1 and 10% w/w, preferably 2.0 and 5.1% w/w microparticles. In another case, the mannitol is provided with a volume average particle size between 10 and 500 μm.

In another embodiment, the excipient comprises lactose for an inhaled dosage form.

In yet another embodiment, the excipient comprises binders, disintegrants, glidants, diluents, color agents, flavoring agents, sweeteners, and lubricants for a solid oral dosage form such as a capsule, a tablet, or a wafer.

For particles to be used in non-pharmaceutical applications, the term "excipient" refers to essentially any material that can be blended with the particles for any purpose.

III. Use of the Particles

Particles made using the processes described herein can be used in a wide variety of applications and industries, including abrasives, agricultural products, biochemical products, chemicals, cosmetics, dyes, foods, metals, pigments, and pharmaceuticals. For some applications, the particles preferably are microparticles.

In a preferred embodiment, the particles are microparticles for use in a pharmaceutical formulation, which can be administered to a human or animal in need thereof, for the delivery of a therapeutic, diagnostic, or prophylactic agent in an effective amount. The formulations can be administered in dry form or dispersed in a physiological solution for injection or oral administration. The dry form can be aerosolized and inhaled for pulmonary administration. The route of administration depends on the pharmaceutical agent being delivered.

In one embodiment, microparticles or blends of microparticles/excipient are jet milled to deagglomerate the particles and then further processed, using known techniques, into a solid oral dosage form. Examples of such solid oral dosage forms include powder-filled capsules, tablets, and wafers. The jet-milling advantageously can provide improved wetting and dispersibility upon oral dosing as a solid oral dosage form formed from these microparticles or microparticle/excipient blends.

The invention can further be understood with reference to the following non-limiting examples.

EXAMPLE 1

Spray Drying of PLGA Microspheres Without Milling (Comparative Example)

This example describes a process for making PLGA microspheres. The microspheres were made in a batch spray drying process. A polymer emulsion was prepared, composed of droplets of an aqueous phase suspended in a continuous polymer/organic solvent phase. The polymer was a commercially obtained poly(lactide-co-glycolide) (PLGA) (50:50). The organic solvent was methylene chloride. The resulting emulsion was spray dried on a custom spray dryer with a dual drying chamber set-up. The process conditions resulted in a theoretical solids to drying gas mass flow ratio of 4.77 g solids/min.:1.6 kg nitrogen/min. The outlet temperature of the primary drying chamber was maintained at 12° C. The discharge of the primary drying chamber was connected to a custom secondary drying chamber comprising 100 feet of 1.5" Ø coiled tubing, enveloped by a water-cooled jacket. The discharge of the secondary drying chamber was connected to a cyclone collector having a 1"Ø inlet, a 1"Ø exhaust outlet, and a 1.5"Ø dust outlet. Three replicate batches were generated. Particle size was measured using a Coulter Multisizer II with a 50 μm aperture. Table 1 presents the average size results for the three batches.

TABLE 1

Particle Size of Unmilled PLGA Microspheres

| Experiment No. | Number Avg. Particle Size, $X_n$ (μm) | Volume Avg. Particle Size, $X_v$ (μm) |
| --- | --- | --- |
| 1.1 | 2.5 ± 0.1 | 6.5 ± 0.1 |

EXAMPLE 2

PLGA Microparticles Formed Using an In-Line Spray Drying/Jet Milling Process

PLGA microspheres were produced using a batch spray drying process with an in-line jet mill. A polymer emulsion was prepared, composed of droplets of an aqueous phase suspended in a continuous polymer/organic solvent phase. The polymer was a commercially obtained poly(lactide-co-glycolide) (PLGA) (50:50). The organic solvent was methylene chloride. The resulting emulsion was spray dried on a custom spray dryer with a dual drying chamber set-up. The process conditions resulted in a theoretical solids to drying gas mass flow ratio of 4.77 g solids/min:1.6 kg nitrogen/min. The outlet temperature of the primary drying chamber was maintained at 12° C. The discharge of the primary drying chamber was connected to a secondary drying chamber comprising 100 feet of 1.5" Ø coiled tubing, enveloped by a water-cooled jacket. The discharge of the secondary drying chamber was connected to a concentrating cyclone having a 1"Ø inlet, a 1"Ø exhaust outlet, and a 1.5"Ø dust outlet. A 0.2 μm filter was attached to each of the concentrating cyclone exhausts. A jet mill (Hosokawa 50AS) was connected to the concentrating cyclone dust outlet using a 1.5"×2" short reducer. Dry nitrogen was supplied to the jet mill for grinding and injection gas. The jet mill was operated at $P_i$=3 bar and $P_g$=2.9 bar. A cyclone collector, having a ⅜" Ø inlet, a ¾" Ø exhaust outlet, and a ¾" Ø dust outlet, was connected to the discharge of the jet mill to collect the microspheres. A 0.2 μm filter was attached to the jet mill cyclone exhaust. This experiment was conducted in triplicate. An average product yield of 56.5±4.2% was obtained. Particle size was measured using the same method as in Example 1, and the average results for the three batches are shown in Table 2.

TABLE 2

Particle Size of In-Line Jet Milled PLGA Microspheres

| Experiment No. | Number Avg. Particle Size, $X_n$ (μm) | Volume Avg. Particle Size, $X_v$ (μm) |
|---|---|---|
| 2.1 | 2.3 ± 0.1 | 4.9 ± 0.1 |

Table 3 provides a comparison of the average size results of the unmilled and in-line milled microspheres from Examples 1 and 2.

TABLE 3

Size Comparison of PLGA Microspheres

| Experiment No. | Number Avg. Particle Size, $X_n$ (μm) | Volume Avg. Particle Size, $X_v$ (μm) |
|---|---|---|
| 1.1 | 2.5 ± 0.1 | 6.5 ± 0.1 |
| 2.1 | 2.3 ± 0.0 | 4.8 ± 0.1 |

This demonstrates that in-line jet milling was effective in deagglomeration.

EXAMPLE 3

Batch Processing of Celecoxib Microspheres (Comparative Example)

Celecoxib (CXB) microspheres were produced using a batch spray drying process. A solution containing CXB in 800 mL of methanol-water (65:35) was spray dried on a custom spray dryer with a single drying chamber. The process conditions resulted in a theoretical solids to drying gas mass flow ratio of 0.24 g solids/min:1.7 kg nitrogen/min. The outlet temperature of the drying chamber was set at 20° C. The discharge of the drying chamber was connected to a cyclone collector having a 1" Ø inlet, a 1" Ø exhaust outlet, and a 1.5" Ø dust outlet.

Duplicate batches were generated. Yield was calculated as the mass of dry product divided by the dry mass of nonvolatile materials in the feed stock. Geometric particle size (volume mean) was measured using an Aerosizer particle sizer set at both high shear and zero shear. Table 4 presents the yield and size results for the two batches.

TABLE 4

Yield and Particle Size Analysis of Unmilled CXB Microspheres

| Experiment No. | Process Yield (%) | Vol. Avg. Particle Size, High Shear, $X_v$ (μm) | Vol. Avg. Particle Size, Zero Shear, $X_v$ (μm) |
|---|---|---|---|
| 3.1 | 68% | 6.2 | 6.0 |
| 3.2 | 76% | 5.4 | 6.3 |
| Avg. | 72% | 5.8 | 6.2 |

The powder from Experiment No. 3.1 was fed manually into a Fluid Energy Aljet Jet-O-Mizer jet mill at a feed rate of about 1 g/min. Dry nitrogen gas was used to drive the jet mill. The operating parameters were 4 bar grinding gas pressure and 8 bar injection gas pressure. A cyclone collector, having a ⅜"×¾" rectangular inlet, a ¾" Ø exhaust outlet, and a ½" Ø dust outlet, was connected to the discharge of the jet mill to collect the microspheres. Yield and particle size were measured using the same methods as described above within the Example. Table 5 compares the results of the pre-milled material (Experiment No. 3.1) to the results of the batch jet milled material (Experiment No. 3.3).

TABLE 5

Comparison of Unmilled and Batch Milled CXB Microspheres

| Experiment No. | Process Yield (%) | Vol. Avg. Particle Size, High Shear, $X_v$ (μm) | Vol. Avg. Particle Size, Zero Shear, $X_v$ (μm) |
|---|---|---|---|
| 3.1 | 68% | 6.2 | 6.0 |
| 3.3 | 77% | 3.3 | 3.4 |

The data shows that jet milling reduced the particle size of the CXB powder. The final yield of the batch process can be calculated by multiplying the yield for experiment 3.1 times the yield from experiment 3.2. This calculates to a final process yield of 52% for the batch milled product.

EXAMPLE 4

Celecoxib Microspheres Formed Using an In-Line Process

CXB microspheres were produced using a spray drying process with an in-line jet mill. A solution containing CXB in 800 mL of methanol-water (65:35) was spray dried on a custom spray dryer with a single drying chamber. The process conditions resulted in a theoretical solids to drying gas mass flow ratio of 0.24 g solids/min.:1.7 kg nitrogen/min. The outlet temperature of the drying chamber was set at 20° C. The discharge of the drying chamber was connected to a concentrating cyclone having a 1" Ø inlet, a 1" Ø exhaust outlet, and a 1.5" Ø dust outlet. A jet mill (Fluid Energy Aljet Jet-O-Mizer) was connected directly to the concentrating cyclone dust outlet. Dry nitrogen was supplied to the jet mill for grinding and injection gas. The jet mill was operated at $P_i$=8 bar and $P_g$=4 bar. This experiment was carried out in duplicate, with different collection cyclones used in each experiment. A cyclone collector, having a ⅜"×¾" rectangular inlet, a ¾" Ø exhaust outlet, and a ½" Ø dust outlet, was connected to the discharge of the jet mill to collect the microspheres for Experiment No. 4.1. A cyclone collector, having a ⅜" Ø inlet, a ¾" Ø exhaust outlet, and a ¾" Ø dust outlet, was connected to the discharge of the jet mill to collect the microspheres for Experiment No. 4.2. The small difference in yield between the two collection cyclones used in Experiments No. 4.1 and No. 4.2 was not considered to be significant. Yield and particle size were measured using the same methods as in Example 3. Table 6 presents the average results for the duplicate batches.

TABLE 6

Yield and Particle Size of In-Line Jet Milled CXB Microspheres

| Experiment No. | Process Yield (%) | Vol. Avg. Particle Size, High Shear, $X_v$ (μm) | Vol. Avg. Particle Size, Zero Shear, $X_v$ (μm) |
|---|---|---|---|
| 4.1 | 64% | 3.5 | 3.3 |

Table 7 provides a comparison of the average size and yield results of the unmilled, batch milled, and in-line milled CXB microspheres from Examples 3 and 4.

TABLE 7

Comparison of CXB Microparticles

| Experiment No. | Final Process Yield (%) | Vol. Avg. Particle Size, High Shear, $X_v$ (μm) | Vol. Avg. Particle Size, Zero Shear, $X_v$ (μm) |
|---|---|---|---|
| 3.2 | 72% | 5.8 | 6.2 |
| 3.3 | 52% | 3.3 | 3.4 |
| 4.1 | 64% | 3.5 | 3.3 |

In-line jet milling was as effective as batch jet milling in reducing particle size. The in-line process resulted in a higher product yield (64%) than the combination of the batch processes (52%).

EXAMPLE 5

Batch Processing of Paclitaxel Microspheres (Comparative Example)

Paclitaxel (PXL) microspheres were produced using a batch spray drying process. A solution containing PXL in 800 mL of ethanol-water (80:20) was spray dried on a custom spray dryer with a single drying chamber. The process conditions resulted in a theoretical solids to drying gas mass flow ratio of 0.83 g solids/min:2.0 kg nitrogen/min. The outlet temperature of the drying chamber was set at 57° C. The discharge of the drying chamber was connected to a cyclone collector having a 1" Ø inlet, a 1" Ø exhaust outlet, and a 1.5" Ø dust outlet.

One batch was generated. Yield was calculated as the mass of dry product divided by the dry mass of non-volatile materials in the feed stock. Geometric particle size (volume mean) was measured using a Mastersizer particle size analyzer set at maximum pressure. Table 8 presents the yield and size results.

TABLE 8

Yield and Particle Size Analysis of Unmilled PXL Microspheres

| Experiment No. | Process Yield (%) | Vol. Avg. Particle Size, $X_v$ (μm) |
|---|---|---|
| 5.1 | 70% | 1.67 |

The powder from Experiment No. 5.1 was fed manually into a Fluid Energy Aljet Jet-O-Mizer jet mill at a feed rate of about 1 g/min. Dry nitrogen gas was used to drive the jet mill. The operating parameters were 4 bar grinding gas pressure and 8 bar injection gas pressure. A cyclone collector, having a ⅜" Ø inlet, a ¾" Ø exhaust outlet, and a ¾" Ø dust outlet, was connected to the discharge of the jet mill to collect the microspheres. Yield and particle size were measured using the same methods as described above within the Example. Table 9 compares the results of the pre-milled material (Experiment No. 5.1) to the results of the batch milled material (Experiment No. 5.2).

TABLE 9

Comparison of Unmilled and Batch Milled PXL Microspheres

| Experiment No. | Process Yield (%) | Vol. Avg. Particle Size, $X_v$ (μm) |
|---|---|---|
| 5.1 | 70% | 1.67 |
| 5.2 | 70% | 1.63 |

The data shows that, in this case, batch jet milling did not significantly change the particle size of the PXL powder. The final yield of the batch process can be calculated by multiplying the yield for Experiment No. 5.1 times the yield from Experiment No. 5.2. This calculates to a final process yield of 49% for the batch milled product.

EXAMPLE 6

Paclitaxel Microspheres Formed Using an In-Line Process

PXL microspheres were produced using a spray drying process with an in-line jet mill. A solution containing PXL in 800 mL of ethanol-water (80:20) was spray dried on a custom spray dryer with a single drying chamber. The process conditions resulted in a theoretical solids to drying gas mass flow ratio of 0.83 g solids/min:2.0 kg nitrogen/min. The outlet temperature of the drying chamber was set at 57° C. The discharge of the drying chamber was connected to a concentrating cyclone having a 1" Ø inlet, a 1" Ø exhaust outlet, and a 1.5" Ø dust outlet. A jet mill (Fluid Energy Aljet Jet-O-Mizer) was connected directly to the concentrating cyclone dust outlet. Dry nitrogen was supplied to the jet mill for grinding and injection gas. The jet mill was operated at $P_i$=8 bar and $P_g$=4 bar. A cyclone collector, having a ⅜" Ø inlet, a ¾" Ø exhaust outlet, and a ¾" Ø dust outlet, was connected to the discharge of the jet mill to collect the microspheres for Experiment No. 6.1. Yield and particle size were measured using the same methods as in Example 5. Table 10 presents the results.

TABLE 10

Yield and Particle Size of In-Line Jet Milled PXL Microspheres

| Experiment No. | Process Yield (%) | Vol. Avg. Particle Size, $X_v$ (μm) |
|---|---|---|
| 6.1 | 66% | 1.46 |

Table 11 provides a comparison of the average size and yield results of the unmilled, batch milled, and in-line milled PXL microspheres from Examples 5 and 6.

TABLE 11

Comparison of PXL Microparticles

| Experiment No. | Final Process Yield (%) | Vol. Avg. Particle Size, High Shear, $X_v$ (μm) |
|---|---|---|
| 5.1 | 70% | 1.67 |
| 5.2 | 70% | 1.63 |
| 6.1 | 66% | 1.46 |

In-line jet milling was more effective than batch jet milling in reducing particle size. The in-line process resulted in a higher product yield (66%) than the combination of the batch processes (49%).

EXAMPLE 7

PLGA Microparticles Formed, Blended with Mannitol/Tween 80, And Jet Milled Using an In-Line Process PLGA microparticles were produced using a single in-line process involving spray drying, blending with Mannitol/Tween 80 powder, and jet-milling using the Hosokawa 50AS jet-mill. A polymer emulsion was prepared, composed of droplets of an aqueous phase suspended in a continuous polymer/organic solvent phase. The polymer was a commercially obtained poly(lactide-co-glycolide) (PLGA) (50:50). The organic solvent was methylene chloride. The resulting emulsion was spray dried on a custom spray dryer with a dual drying chamber set-up. The Mannitol/Tween 80 powder was injected at the discharge of the secondary drying chamber (which is upstream from the concentrating cyclone having a 1" Ø inlet, a 1" Ø exhaust outlet, and a 1.5" Ø dust outlet) using a nitrogen feed. The dust outlet of the concentrating cyclone was connected to the inlet of the jet-mill. Another cyclone collector, having a 1" Ø inlet, a 1" Ø exhaust outlet, and a 1.5" Ø dust outlet, was connected to the discharge of the jet-mill to collect the product.

The experiment was conducted in duplicate. The particle size of the product obtained from this experiment is given in Table 12.

TABLE 12

Particle Size Results

| Experiment No. | Number Avg. Particle Size, $X_n$ ($\mu$m) | Volume Avg. Particle Size, $X_v$ ($\mu$m) |
|---|---|---|
| 7.1 | 2.2 ± 0.06 | 5.3 ± 0.15 |
| 7.2 | 2.2 ± 0.06 | 5.5 ± 0.20 |

Three samples from Experiment No. 7.1 were reconstituted with 5 ml of RO/DI water, which dissolved the Mannitol/Tween 80 powder. The microsphere mass for each vial was determined by filtering the reconstituted suspension and collecting the undissolved microspheres on the filter. The mass of mannitol/Tween 80 was determined by lyophilizing the filtered solution. The results are given in Table 13.

TABLE 13

Particle Size Results

| Experiment No. | PLGA microsphere mass (mg) | Mannitol/Tween 80 mass (mg) |
|---|---|---|
| 7.1, vial #1 | 206 | 220 |
| 7.1, vial #2 | 234 | 223 |
| 7.1, vial #3 | 216 | 232 |
| Average ± S.D. | 219 ± 14 | 225 ± 6 |
| R.S.D. | 6.4% | 2.8% |

The relative standard deviation (R.S.D.) values from the Table 13 indicate that it was possible to achieve a uniform blend through an in-line process involving spray drying, blending, and jet milling.

Publications cited herein and the materials for which they are cited are specifically incorporated by reference. Modifications and variations of the methods and devices described herein will be obvious to those skilled in the art from the foregoing detailed description. Such modifications and variations are intended to come within the scope of the appended claims.

We claim:

1. An apparatus for making particles comprising:
   at least one atomizer for spraying an emulsion, solution, or suspension which comprises a solvent and a bulk material to form droplets of the solvent and the bulk material;
   a primary drying chamber having a drying gas inlet and a discharge outlet, the atomizer being located in the primary drying chamber which provides for evaporation of at least a portion of the solvent into the drying gas to solidify the droplets and form particles dispersed in the drying gas; and
   an inline jet mill having an inlet in fluid communication with the discharge outlet primary drying chamber, the jet mill being operable to receive the particles dispersed in at least a portion of the drying gas and grind or deagglomerate the particles, wherein the jet mill comprises a spiral jet mill or other fluid energy impact mill.

2. The apparatus of claim 1, further comprising at least one secondary drying chamber interposed between, and in fluid communication with, the discharge outlet of the primary drying chamber and the inlet of the jet mill, wherein the at least one secondary drying chamber provides for evaporation of a second portion of the solvent into the drying gas.

3. The apparatus of claim 2, wherein the at least one secondary drying chamber comprises tubing having an inlet in fluid communication with the discharge outlet of the primary drying chamber, wherein the ratio of the cross-sectional area of the primary drying chamber to the cross-sectional area of the tubing is at least 4:3, and wherein the ratio of the length of the tubing to the length of the primary drying chamber is at least 2:1.

4. The apparatus of claim 1, further comprising a particle concentration means, interposed between, and in fluid communication with, the primary drying chamber and the inline jet mill, to separate and remove at least a portion of the drying gas from the particles.

5. The apparatus of claim 4, wherein the particle concentration means comprises a cyclone separator.

6. The apparatus of claim 4, wherein the particle concentration means comprises one or more devices selected from the group consisting of gravity settling chambers, electrostatic charge precipitators, impingement separators, mechanical centrifugal separators, and uniflow cyclones.

7. The apparatus of claim 4, further comprising a flow controlling device to control the flow rate of drying gas discharged from the particle concentration means.

8. The apparatus of claim 7, wherein the flow controlling device comprises a device selected from the group consisting of control valves, filters, regulators, orifices, and combinations thereof.

9. The apparatus of claim 1, further comprising a collection cyclone which separates the drying gas from the deagglomerated or ground particles discharged from the jet mill.

10. The apparatus of claim 9, further comprising a flow controlling device to control the flow rate of the drying gas discharged from the collection cyclone.

11. The apparatus of claim 10, wherein the flow controlling device comprises a device selected from the group consisting of control valves, filters, regulators, orifices, and combinations thereof.

12. The apparatus of claim 1, further comprising a means for introducing an excipient material into the particles and drying gas flowing between the discharge outlet of the primary drying chamber and the inlet of the jet mill.

13. The apparatus of claim 1, comprising a plurality of atomizers disposed in the primary drying chamber.

14. An apparatus for making microparticles comprising:
   at least one atomizer for spraying an emulsion, solution, or suspension which comprises a solvent and a bulk material to form droplets of the solvent and the bulk material;
   a primary drying chamber having a drying gas inlet and a discharge outlet, the atomizer being located in the primary drying chamber which provides for evaporation of at least a portion of the solvent into the drying gas to solidify the droplets and form microparticles dispersed in the drying gas;

an inline jet mill having an inlet in fluid communication with the discharge outlet primary drying chamber, the jet mill being operable to receive the microparticles dispersed in at least a portion of the drying gas and to grind or deagglomerate the microparticles; and at least one secondary drying chamber interposed between, and in fluid communication with, the discharge outlet of the primary drying chamber and the inlet of the jet mill, wherein the at least one secondary drying chamber provides for evaporation of a second portion of the solvent into the drying gas.

15. The apparatus of claim 14, further comprising at least one cyclone separator which separates and removes at least a portion of the drying gas from the microparticles.

16. An apparatus for making particles in a continuous process comprising:

at least one atomizer for spraying an emulsion, solution, or suspension which comprises a solvent and a bulk material to form droplets of the solvent and the bulk material;

a primary drying chamber having a drying gas inlet and a discharge outlet, the atomizer being located in the primary drying chamber which provides for evaporation of at least a portion of the solvent into the drying gas to solidify the droplets and form particles dispersed in the drying gas;

an inline, spiral jet mill having an inlet in fluid communication with the discharge outlet primary drying chamber, the jet mill being operable to receive the particles dispersed in at least a portion of the drying gas and grind or deagglomerate the particles;

a cyclone separator, interposed between, and in fluid communication with, the primary drying chamber and the inline jet mill, to separate and remove at least a portion of the drying gas from the particles;

a collection cyclone which separates the drying gas from the deagglomerated or ground particles discharged from the jet mill; and a first flow controlling device to control the flow rate of the drying gas discharged from the cyclone separator or the collection cyclone.

17. The apparatus of claim 16, further comprising a second flow controlling device to control the flow rate of the drying gas discharged from the cyclone separator or the collection cyclone, whichever is not controlled by the first flow controlling device.

* * * * *